United States Patent
Robinson et al.

(10) Patent No.: US 12,128,202 B1
(45) Date of Patent: Oct. 29, 2024

(54) DISPOSABLE TOPICAL APPLICATION SYSTEM

(71) Applicants: Nena Robinson, Atlanta, GA (US); Tyndal Clark, Atlanta, GA (US)

(72) Inventors: Nena Robinson, Atlanta, GA (US); Tyndal Clark, Atlanta, GA (US)

(*) Notice: Subject to any disclaimer, the term of this patent is extended or adjusted under 35 U.S.C. 154(b) by 0 days.

(21) Appl. No.: 16/949,663

(22) Filed: Nov. 9, 2020

Related U.S. Application Data (60) Provisional application No. 62/933,115, filed on Nov. 8, 2019.

(51) Int. Cl.
*A61M 35/00* (2006.01)
*A45D 34/04* (2006.01)

(52) U.S. Cl.
CPC ......... *A61M 35/003* (2013.01); *A45D 34/042* (2013.01); *A45D 2200/054* (2013.01)

(58) Field of Classification Search
CPC .............. A61M 35/003; A61M 35/006; A45D 2200/1045; A45D 34/04; A45D 34/042; A45D 34/043; A45D 34/044; A45D 34/045; A45D 40/26; A45D 40/262; A45D 40/263; A45D 40/264; A45D 40/265; A45D 2200/1018; A46B 11/0041; A46B 11/0075; A46B 11/0003; A46B 11/0027; A46B 2200/1066; B43M 11/06; B43K 5/14; B43K 5/18
See application file for complete search history.

(56) References Cited

U.S. PATENT DOCUMENTS

| | | | | |
|---|---|---|---|---|
| 2,386,085 A * | 10/1945 | Babel | ............ | A46B 17/00 15/104.94 |
| 3,792,699 A * | 2/1974 | Tobin | ............ | B01L 3/5029 401/133 |
| 4,206,843 A * | 6/1980 | Rainey | ............ | A61M 35/006 604/3 |
| 4,620,648 A * | 11/1986 | Schwartzman | ............ | B65D 47/44 137/844 |
| 4,740,194 A * | 4/1988 | Barabino | ............ | A61F 13/38 604/3 |
| 5,006,004 A * | 4/1991 | Dirksing | ............ | A45D 34/042 401/265 |
| 6,773,189 B1 * | 8/2004 | Tsaur | ............ | B43M 11/06 604/3 |
| 10,687,601 B2 * | 6/2020 | Rosario-Melendez | .. | A61K 8/92 |
| 2008/0142032 A1 * | 6/2008 | Liberty | ............ | A45D 33/06 132/200 |

(Continued)

*Primary Examiner* — Guy K Townsend
*Assistant Examiner* — Peter Daniel Smith (57) ABSTRACT

A disposable topical application system having a substantially flexible and separable sterile container having a dispensable product, and a sterile applicator. The separable container formed of two major sections, such that the dispensable product is in the first section and the applicator in the second section. A fluid communication defined between the first and section sections. The second section being separable from first section, thus exposing the applicator. Application of gentle manual force pushes the dispensable product from the first section to the application, via the fluid communication therein. The dispensable product, such as lip gloss, lotion, and the like, contained in the container, is thereby permitted to flow through from the first section into the applicator.

4 Claims, 12 Drawing Sheets

(56) References Cited

U.S. PATENT DOCUMENTS

2016/0257470 A1* 9/2016 Casey .................. A45D 34/042
2016/0262524 A1* 9/2016 San Miguel ......... A45D 40/265
2018/0202595 A1* 7/2018 Lahousse ............. C08G 77/442

* cited by examiner

DISPOSABLE TOPICAL APPLICATION SYSTEM

REFERENCE TO RELATED APPLICATIONS

This application claims priority to Provisional Utility Patent Application No. 62/933,115 filed on Nov. 8, 2019. Provisional Utility Patent Application No. 62/933,115 is incorporated by reference herein. Applicant claims the earlier filing date.

TECHNICAL FIELD OF THE INVENTION

The technology described herein relates to the fields of applicators for dispensable products for consumers. More specifically, the invention is a disposable topical application system which allows a user to efficiently apply dispensable products from a sterile and disposable container to the person of the user or other surface. Alternatively, said system can be adapted to prevent inadvertent dispensing and be refillable for multiple uses prior to discarding.

BACKGROUND OF THE INVENTION

As the number of medications, dispensable products, cosmetics, and dispensable products on the market today continues to increase, users are looking for more effective and convenient methods or systems for applying such products. In particular, users gravitate towards cost-effective applicators that make it easy to dispense a desired amount or amount and then to apply this amount to a portion of the body or other surface in a sterile and sanity manner. In addition, with medicinal products, ensuring a user does not over-dose and under-dose is accomplished by controlling the amount dispensed in the disposable container. With the rising costs of cosmetics, the disposable topical application system permits cosmetic companies with expensive products to introduce their products at lower costs in a single use application to attract the average consumer to their cosmetics. Thus, users are looking for a cost-effective applicator that allows them to easily apply an appropriate amount or amount of medication, cosmetics, and other dispensable products in an efficient and sterile manner.

SUMMARY OF THE INVENTION

The present invention is a hand-held application system for applying a dispensable product, such as a pharmaceutical product, to skin or other area of the body. The applicator is in the form of a brush, sponge, dropper, or substantially flat substrate having a front side and an opposing rear side. At least one of the sides defines a sterile dosing area corresponding to at least one recommended amount of the dispensed product. The product is applied to the targeted area, for example, by forcing or squeezing the product from a container. A user then wipes or dabs the sterile applicator containing the product therein, onto a targeted area of the skin.

The present invention also encompasses the combination assembly of a dispensable product, sterile container, and a sterile applicator for administering at least one recommended amount of the product. The product is retained in a dispensing package and the applicator is comprised of a brush, sponge, dropper, or substrate having a front side and an opposing rear side, the front side defining an area corresponding to at least one recommended amount of the dispensable product. In particular, the assembly comprises a container housing a dispensable product and an applicator for administering at least one recommended amount of the dispensable product. The applicator comprises a substrate having a substantially flat front side and an opposing substantially flat rear side, such as a spatula. The front side defines a sterile dosing area corresponding to at least one recommended amount of the dispensable product and the front side is comprised of a material adapted to retain the dispensable product without causing the dispensable product to substantially stick to the surface of the front side and adapted to not substantially change a chemical property of the dispensable product.

The present invention also encompasses a sterile applicator for topically applying to the skin a dispensable product comprising ointments, salves, drops, gels, liquid bandages, or other fluid medicinal products.

The present invention also encompasses a sterile applicator for topically applying to the body a dispensable product comprising nail polish, lipsticks, lip gloss, eyeliner, lip liner, ointments, makeup, teeth whiteners, lotion, skin creams, or any fluid cosmetic products.

The present invention also encompasses a sterile applicator for applying to any surface a dispensable product comprising glue, condiments, toothpaste, deodorants, sauces, jellies, or other fluid products.

The present invention also encompasses a method of using the aforementioned applicators. In particular, the method comprises disposing the product in a first area, if the product is to be applied to one portion of the body, and disposing the pharmaceutical product in the first area and a second area, if the pharmaceutical product is to be applied to an alternate portion of the body and placing the disposed product on an affected area of the body.

The present invention further contemplates a combination assembly intended to be used for housing a dispenser containing a dispensable product the ("primary container"), said assembly comprising: a carton for receiving the primary container or containers; an applicator or a plurality of applicators which are integral with the carton, and optionally an information-bearing insert.

The invention also includes the assembly after being filled with the primary container or containers, i.e. the assembly comprising: a carton, at least one primary container housed within the carton, an applicator or plurality of applicators of the invention which are integral with the carton, and optionally an information-bearing insert.

Various applicators for dispensing fluid compositions have been introduced in the prior art. According to a common design approach, an applicator includes a container that is filled with a fluid or paste to be dispensed. A seal encloses a cavity that holds a fluid composition at the proximate end of a container. A severable cap crowns the container and covers the proximate end of the applicator. A porous or flat tip of an applicator is extendable from the distal end of the container and facilitates egress of the liquid or fluid contents of the container there through, thus allowing the contents to impregnate the applicator tip. Hence, the present invention is intended to improve disposable applicators. A more efficient and inexpensive disposable topical application system that is sterile and convenient is ideally needed.

BRIEF DESCRIPTION OF THE DRAWINGS

APPENDIX A contains an abstract and addendum to the specification.

DETAILED DESCRIPTION OF CERTAIN EMBODIMENTS

Detailed embodiments of the present invention are disclosed herein. However, it is to be understood that the disclosed embodiments are merely exemplary of the invention which may be embodied in various forms. Therefore, specific structural and functional details disclosed herein are not to be interpreted as limiting, but merely as a basis for subsequent claims and as a representative example for teaching one skilled in the art to variously employ the present invention in virtually any appropriately detailed structure. Reference is now made to the drawings. Features will be described here for the purposes of correlation to the referred drawings.

The preferred embodiment of the disposable topical application system 10 teaches a front side that is industrially coupled to a rear side. Preferred coupling methods will be discussed later. The die-cut sides have corresponding contoured areas that create a first cavity 18 in the assembled container to accommodate the proximate end 17 of the applicator (tip) 14 and a second cavity 22 to define the fluid-holding portion 15 of the disposable topical application system 10. A generally cylindrical elongated applicator 16 with a central bore is introduced between the respective sides prior to joinder to form the assembled container. The composition of the sides and applicator and construction of the preferred embodiment of the invention are generally discussed in Appendix A without limiting thereto herein below.

Figure 1:
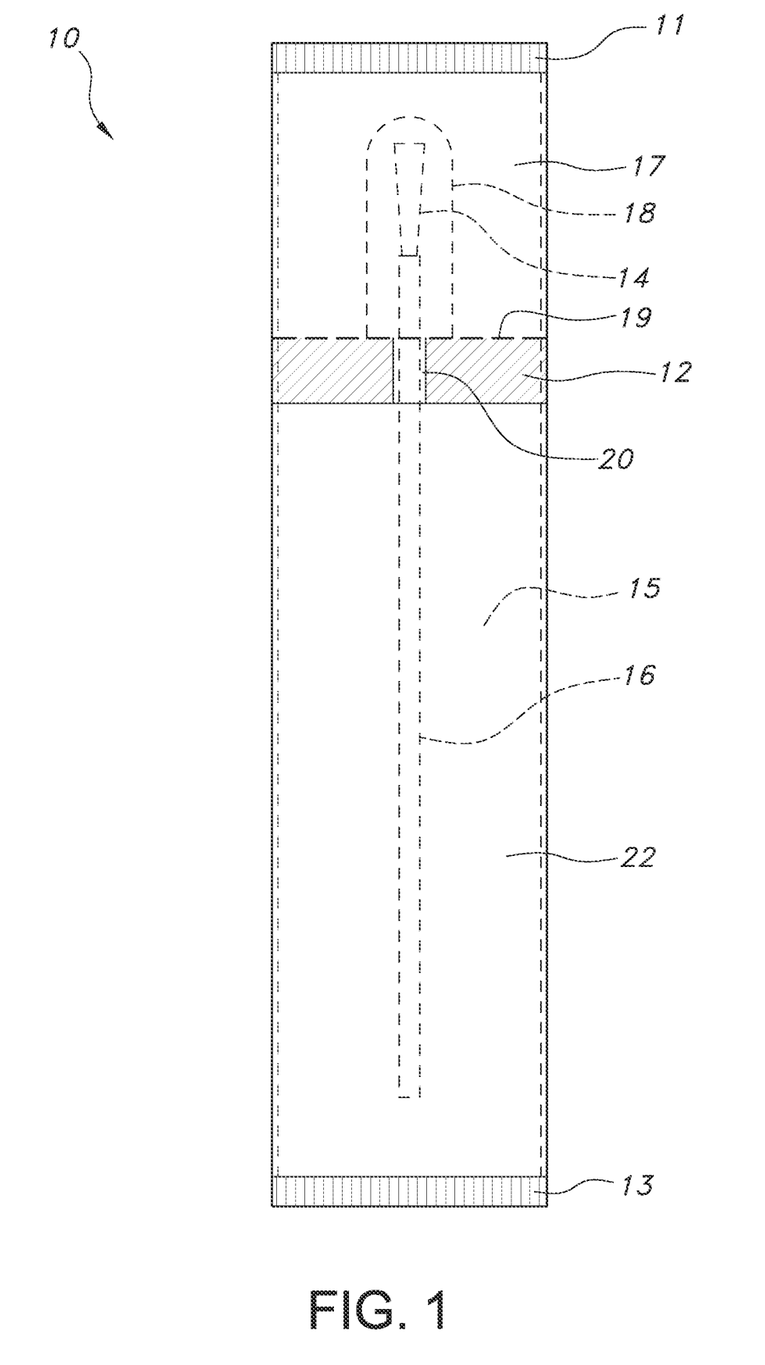
FIG. 1 is front sectional view of the disposable topical application system of the present invention where the container is charged with a dispensable product.
Figure 2:
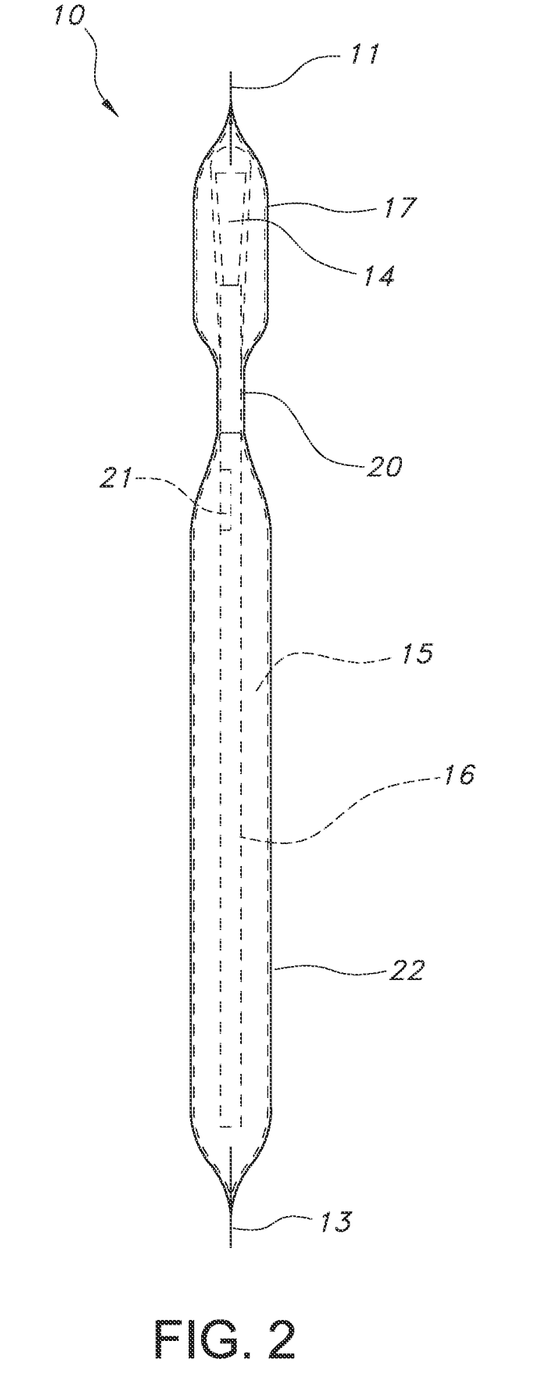
FIG. 2 is a side sectional view of the disposable topical application system of the present invention.
Figure 3:
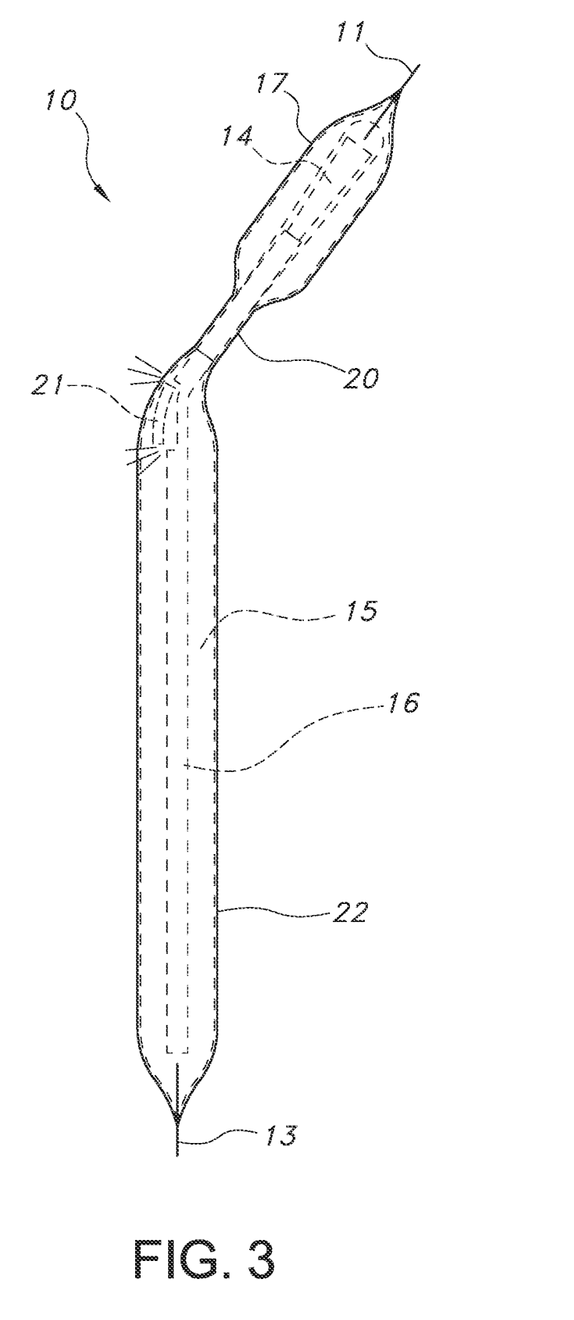
FIG. 3 is a side sectional view of the disposable topical application system of the present invention upon rupturing the containment seal.
Figure 4:
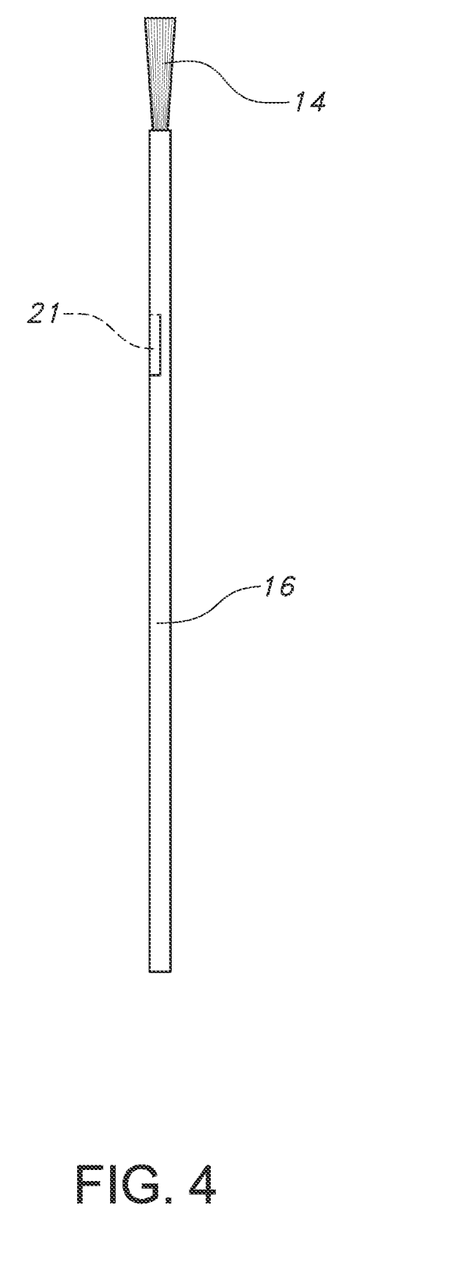
FIG. 4 is a side sectional view of the applicator of the disposable topical application system of the present invention.
Figure 5:
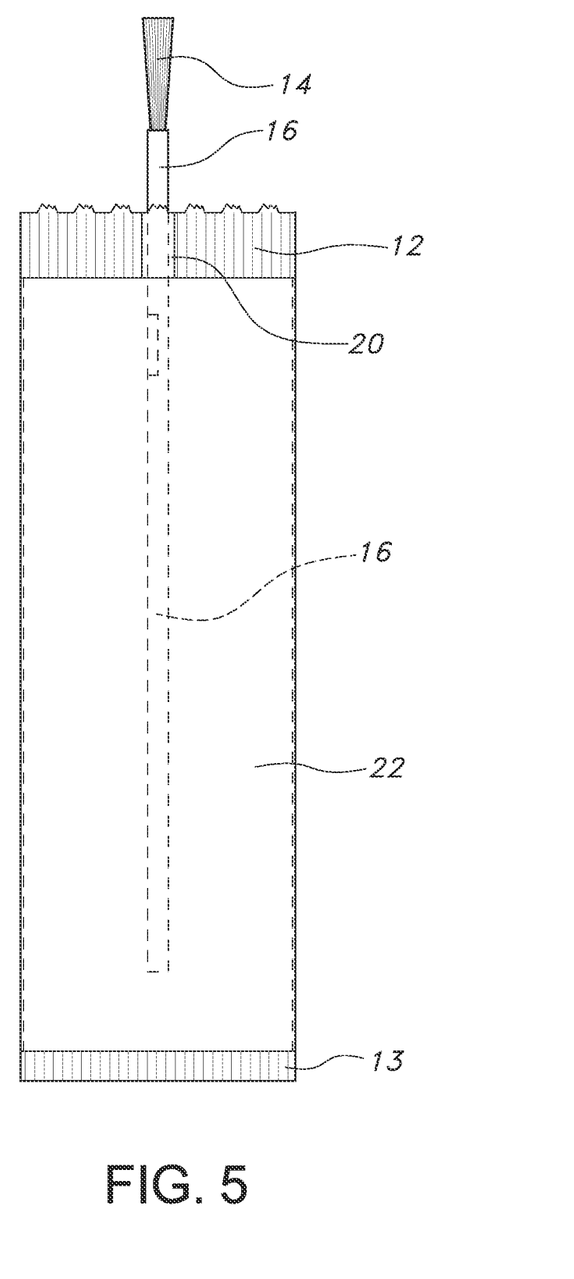
FIG. 5 is a front sectional view of an unsealed disposable topical application system of the present invention.

Referring to FIGS. 1-8, a disposable topical application system 10 is constructed in accordance with a first embodiment of the invention. The disposable topical application system 10 comprises a sterile container that contains a dispensable product 15, including but not limited to a fluid, paste, gel, or other fluid composition to be dispensed and an integral sterile applicator 14. The top 17 of the container 10 is formed with a neck portion 12 that is generally rectangular as seen in FIGS. 1-3 but need not be limited to any particular shape or size as long as it is capable of enclosing the proximate end 20 of the elongated applicator 16 as described in further detail below. The neck portion 12 is severably attached to the portion 22 of the container 10 that stores the dispensable product 15. This coupling can be accomplished in several ways, but the preferred embodiment teaches a perforated arrangement 19 that is easily ruptured with the application of proper manual force by a user. As best seen in FIGS. 1 and 5, that line of perforation 19 horizontally spans across the width of the body of the disposable topical application system 10. As seen in FIG. 3, prior to the removal (or thereafter) of the neck portion 20 of the container 10, the elongated applicator 16 is manipulated to cause an acute bend at the proximate end 20 of the applicator 16 near the top of the fluid-holding portion 22 of the container 10. The elongated applicator 16 features an aperture at the apex of the bend, which is discussed in further detail below. The aperture is sealed with a frangible or comprisable cover 21. This cover 21 can be constructed from any number of materials and adhesively applied to cover the aperture, for instance. When the elongated applicator 16 is subjected to a forcible bend by a user, the seal created by said cover 21 is permanently ruptured and the aperture is exposed, thus facilitating the introduction of the dispensable product 15 into said applicator, which shall be discussed in further detail below. Once the seal is ruptured, the user applies additional force to sever the neck portion 12 from the rest of the container 10 along the line of perforation 19. At this point, the proximate end 20 of the applicator 16 is exposed. The contents 15 of the disposable topical application system 10 can be selectively dispensed by the user in a sterile manner.

In a sealed state, the container 10 of the disposable topical application system extends downwardly from the neck portion 12 and congruously therewith having a pair of flexible walls 22 with the aforementioned second cavity 15 that form a fluid-holding body portion 22 of the container 10. As best seen in FIG. 1, the container 10 is generally rectangular in one dimension. However, this configuration is exemplary only and it should be understood that the fluid-holding body portion 22 of the container 10 can be constructed according to any desired shape and size. The container 10 can have any desired rigidity depending on whether it is to be squeezable and flexible (or resistant to squeezing in rigid alternative embodiments) and can be made from any suitable material that has the desired rigidity and is impervious to the fluid contents. Exemplary materials include aluminum, plastic polymer materials, etc. When the container 10 has a configuration such as that shown in FIGS. 1-3, it will ideally be designed to have medium rigidity. Medium rigidity would be provided by molding the container 10 from a material such as moderately flexible plastic conducive to squeezing. High rigidity would be provided by forming the container 10 from glass or metal materials, thus impeding squeezing and requiring a different means to cause the fluids to exit the container 10. Furthermore, if a container with a very low rigidity is desired, an alternative container design could be used, such as a flexible pouch made from leak-proof fabrics, synthetic materials, or the like. Many other alternative constructions would also be possible.

The neck portion 12 and fluid-holding portion 22 of the container 10 are ideally formed from paired flexible walls having a front side that corresponds to a rear side where the edges are heat-sealed, ultrasonically welded, joined by adhesives, or any suitable means of construction consistent with the preferred embodiment of the invention. The aforementioned first cavity 18 accommodates the brush end of the applicator in the preferred embodiment.

The dispensable product or fluid is efficiently introduced to the fluid-holding portion of the disposable topical application system by industrial means. Once the container 10 is formed and sealed, ultrasonically welded, joined by adhesives, or any suitable means of construction consistent with the preferred embodiment of the invention. The aforementioned first cavity 18 accommodates the brush end of the applicator in the preferred embodiment.

A sealed edge of suitable configuration extends across the top of the body of the fluid-holding portion 22 with only an opening formed by the neck portion 12 or distal end of the elongated applicator 16 and provides an upper barrier to the fluid within the container 10 as defined by the aforementioned second cavity. A central fluid delivery aperture in the wall of the cylindrical applicator provides a fluid pathway out of the fluid-holding portion 22 of the container 10 the central bore of the applicator 16. The aperture is strategically disposed at the neck of the applicator 16 near to the top edge seal, so as to encourage maximum dispensing with the introduction of gravity when the disposable topical application system is inverted for use. The elongated applicator 16 is generally tubular in shape so as to define a central fluid passage. The distal end of the applicator 16 features an aperture capable of permitting the passage of fluid therein. In the preferred embodiment, the contents of the container 10 pass through the aforementioned aperture and subsequently impregnate the tip 14 of the application. Depending on the construction of the applicator 16, the portion of the applicator 16 in the sealed container aids manual dexterity when the disposable topical application system 10 is in use.

Figure 6:
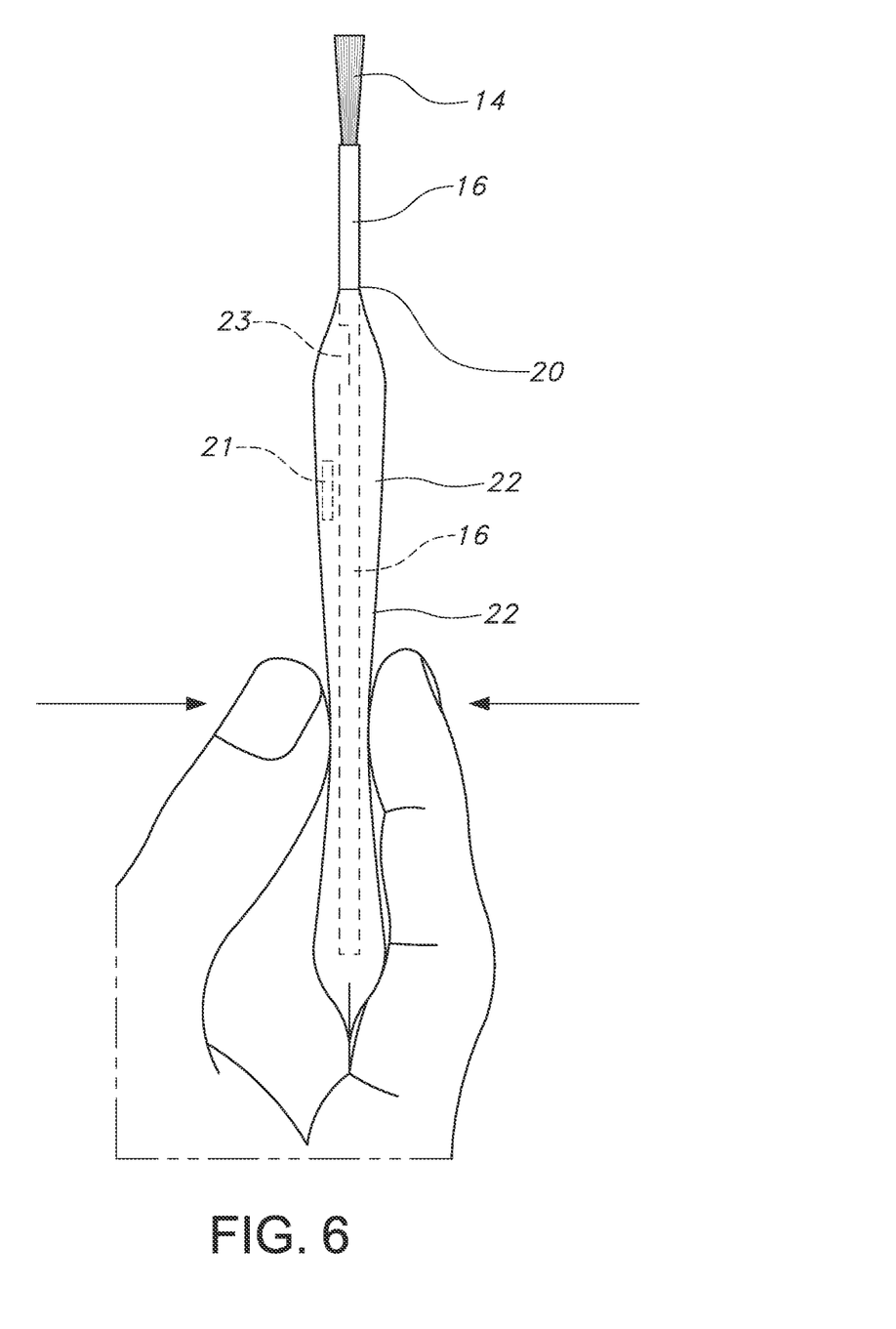
FIG. 6 is a side sectional view of an unsealed disposable topical application system of the present invention being manipulated by the user.
Figure 7:
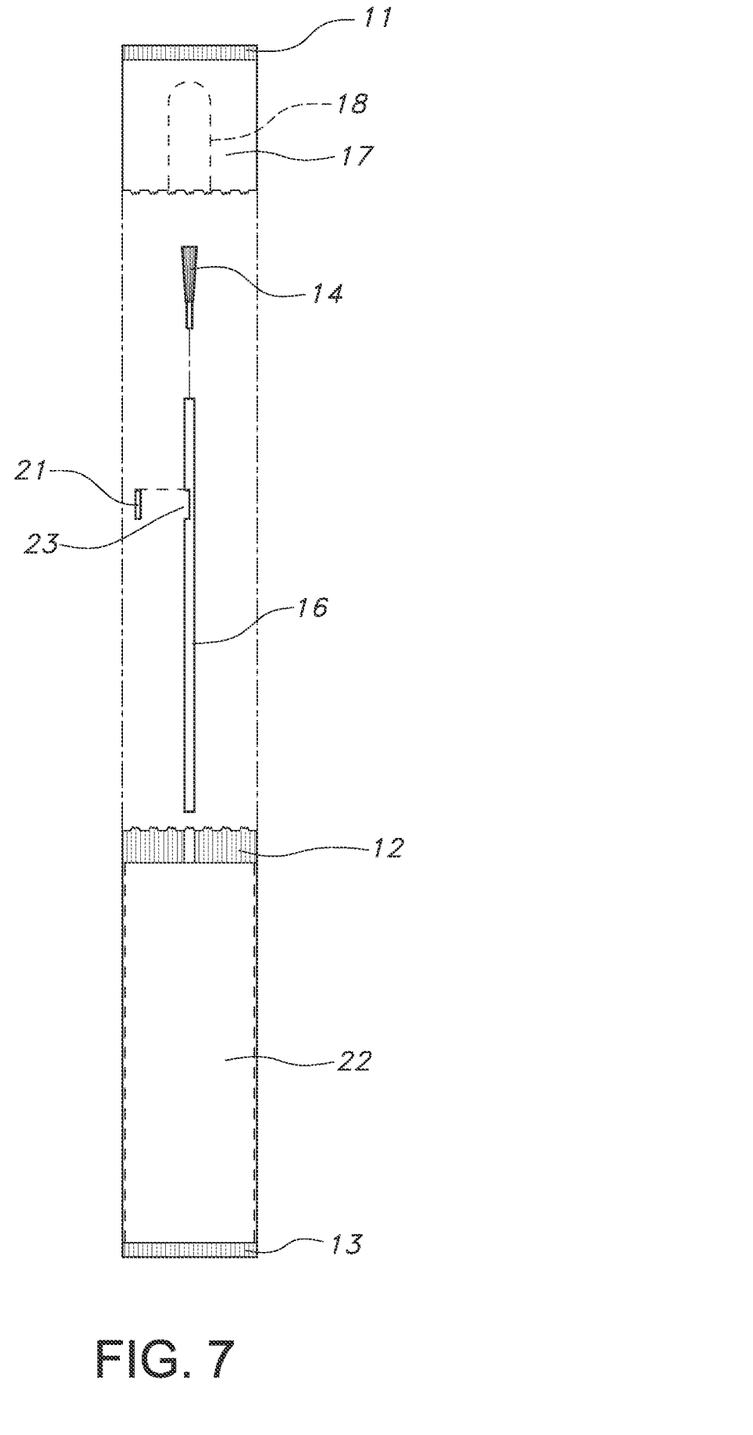
FIG. 7 is a front exploded view of an unsealed disposable topical application system of the present invention.
Figure 8:
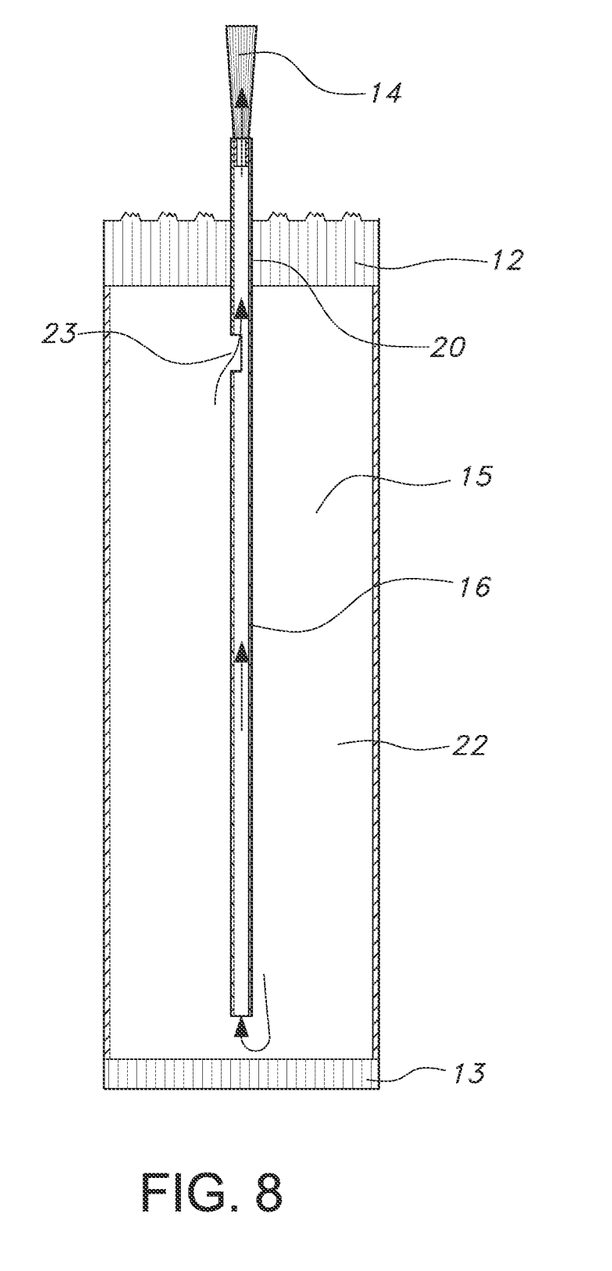
FIG. 8 is a front sectional view of showing the egress of the contents of an unsealed disposable topical application system of the present invention.
Figure 10:
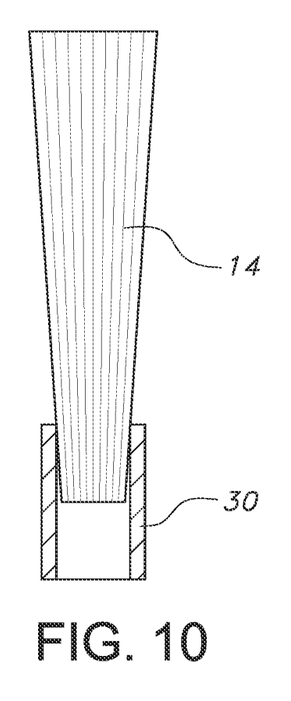
FIG. 10 is a side sectional view of a bristle tip applicator of the disposable topical application system of the present invention.
Figure 11:
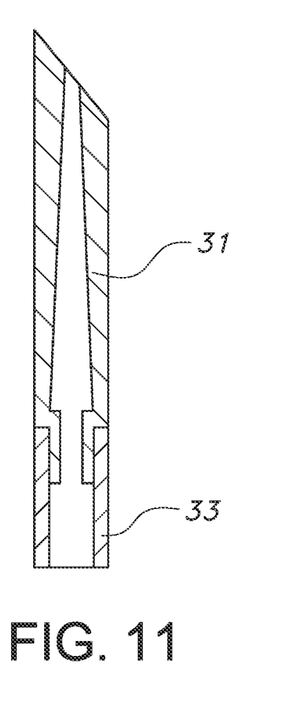
FIG. 11 is a side sectional view of a spatula tip applicator of the disposable topical application system of the present invention.
Figure 12:
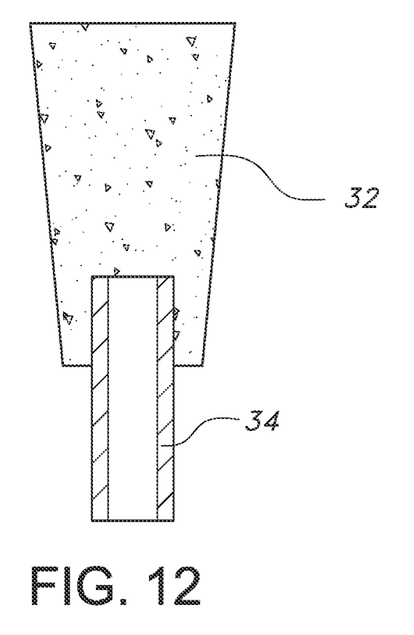
FIG. 12 is a side sectional view of a sponge tip applicator of the disposable topical application system of the present invention.
Figure 13:
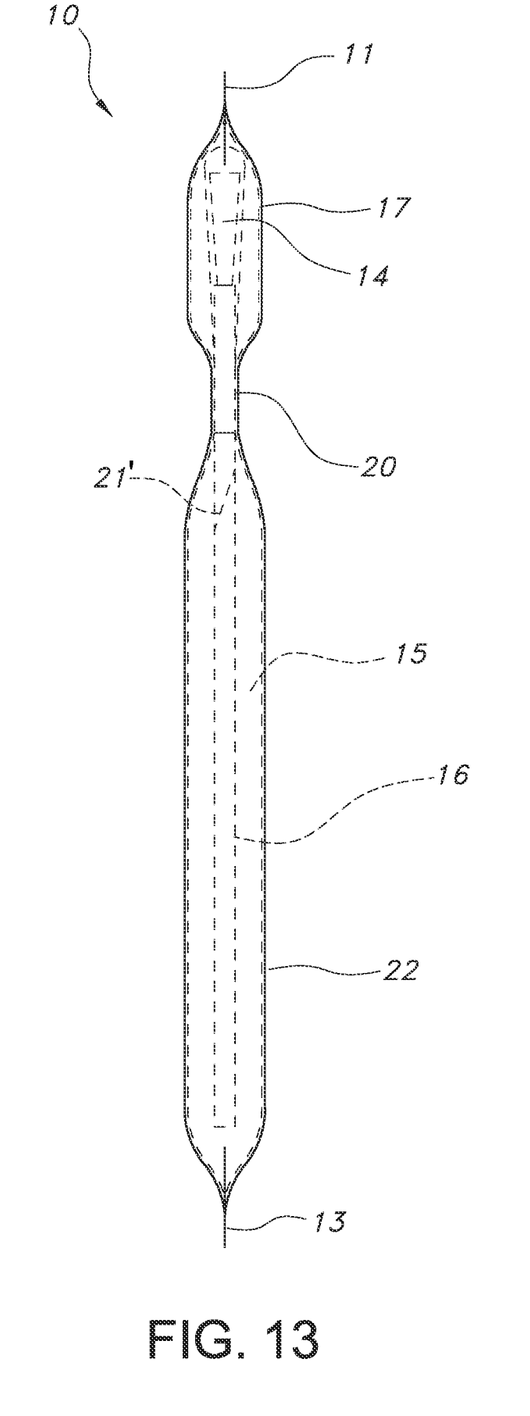
FIG. 13 is a side sectional view of an alternative embodiment of the disposable topical application system of the present invention.
Figure 14:
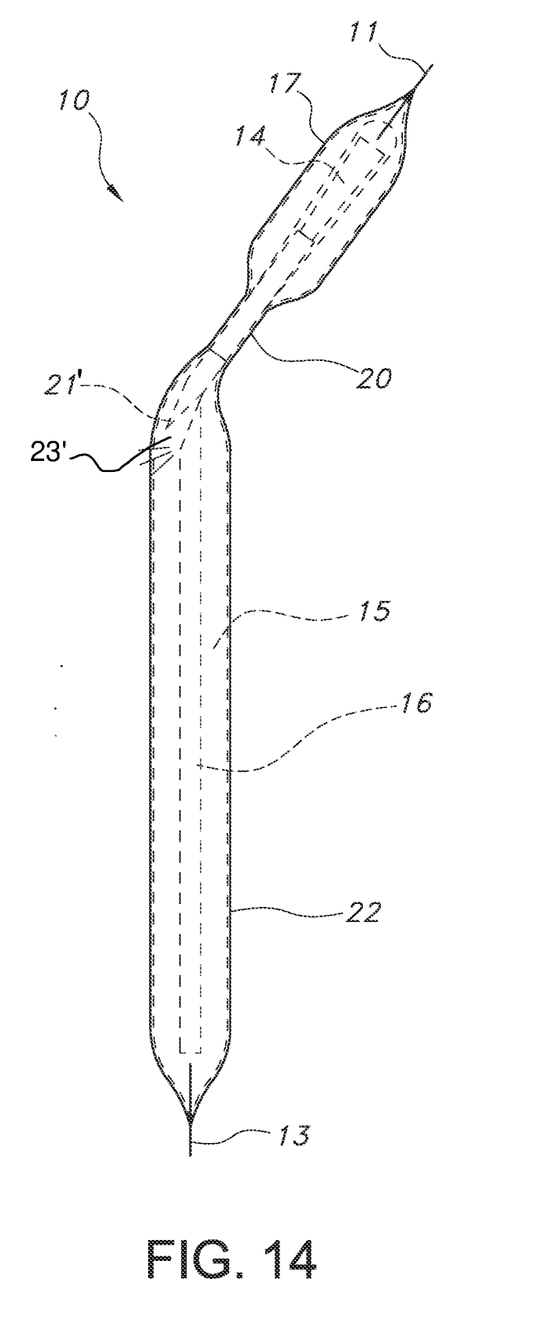
FIG. 14 is a side sectional view of an alternative embodiment of the disposable topical application system of the present invention upon rupturing the containment seal.
Figure 15:
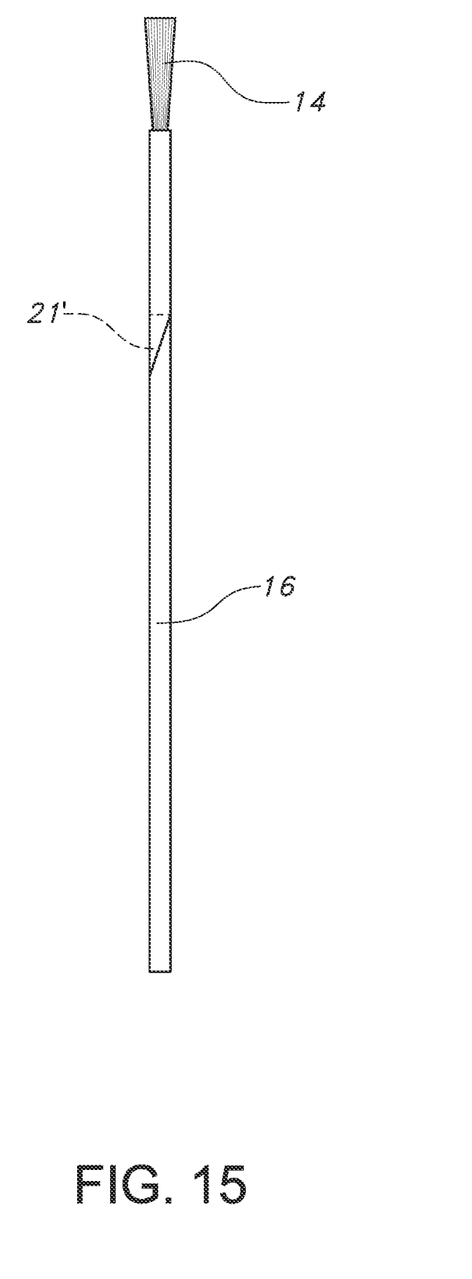
FIG. 15 is a side sectional view of the applicator of an alternative embodiment of the disposable topical application system of the present invention.
Figure 16:
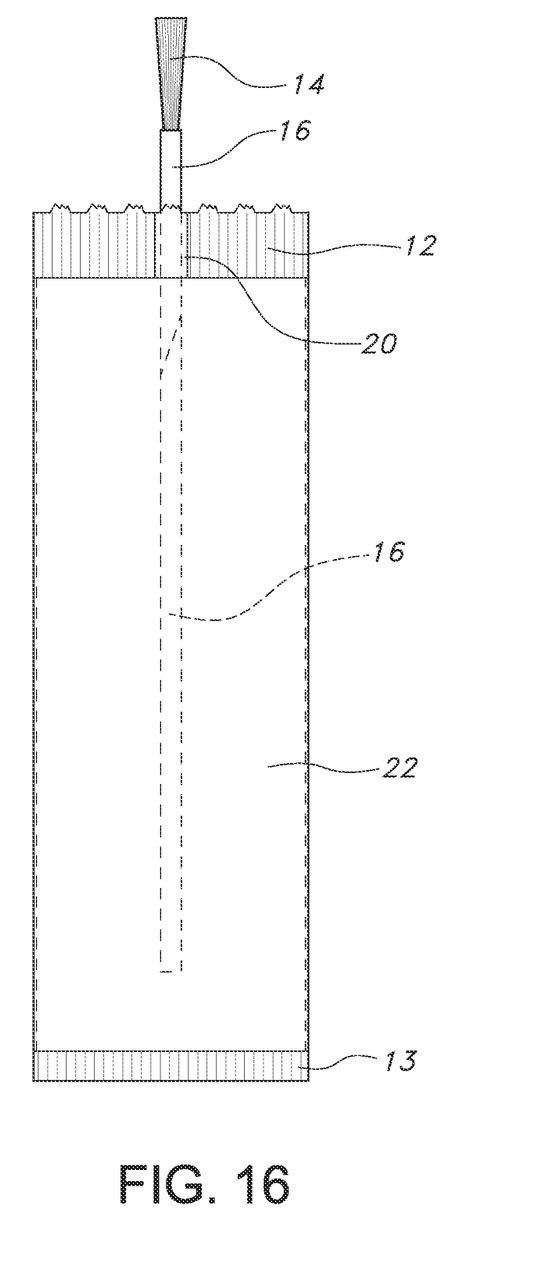
FIG. 16 is a front sectional view of an unsealed alternative embodiment of the disposable topical application system of the present invention.
Figure 17:
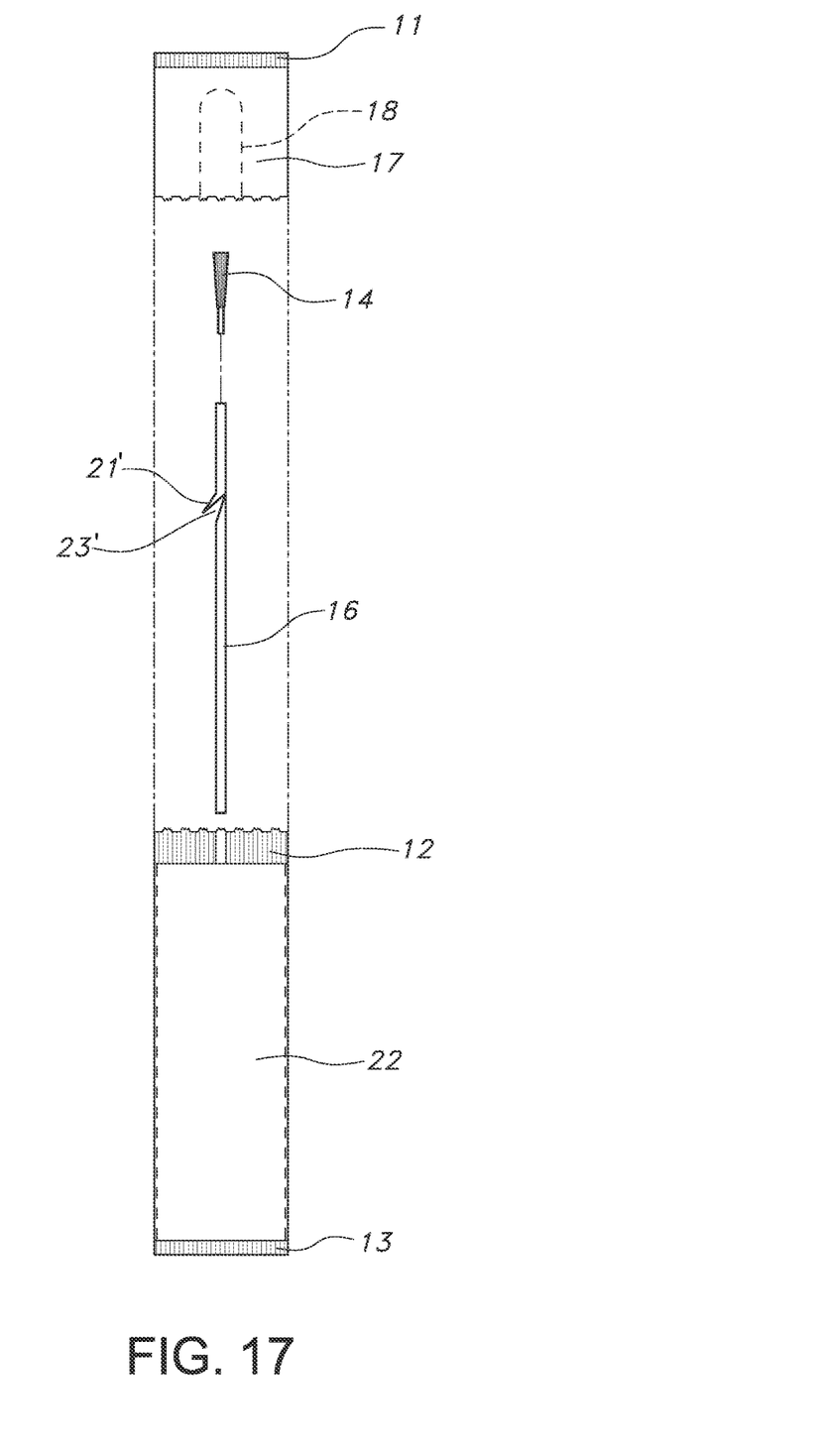
FIG. 17 is a front exploded view of an unsealed alternative embodiment of the disposable topical application system of the present invention.

A generally diverse applicator tip 14 can be conveniently formed at the proximate end 20 of the hollowed applicator 16 secured within the container 10 by sealing the top edge 12 of the fluid-holding portion 22 using a suitable lamination or other bonding process. As seen in FIGS. 1-10, the preferred embodiment teaches a tip having a brush configuration defined by a plurality of bristles. As seen in FIG. 6, once urged from the fluid-holding portion 22 via manual force or squeezing (as shown by the opposing arrows), the fluid is urged through the aperture in the applicator and subsequently impregnates the brush tip upon exit the proximate end 20 (or 30 as seen in FIG. 10) of the applicator as seen in FIG. 8. Inclusion of various tip configurations which might include the use of additional mounting arrangements 33 or 34 for a spatula tip 31 or sponge tip 32 are shown in FIGS. 11 and 12, respectively. The applicator tip 14 receives the fluid via the fluid pathway provided by the aperture. The applicator tip 32 is sufficiently porous to the fluid and can be formed as a foam member using a suitable polymeric (e.g., urethane) open cell foam. Moreover, the applicator tip 14 can be fashioned as a dropper (not shown) for precision placement of the dispensable product (e.g., eye drops).

Once the tip 14, 31, or 32 is impregnated, the dispensable product can be used for any purpose including medical applications (e.g., treating a wound), business applications (e.g., typographic correction), cosmetic applications (e.g., nail polish), condiment applications (e.g., spreading butter on toast), or industrial applications (e.g., lubrication). The only limitation on the dispensable product is compatibility with the materials used to construct the applicator system 16, and that its viscosity is not so great that it prevents dispensing from the elongated applicator 16 under normal use conditions. For instance, if the disposable topical application system 10 is used to apply a dosage of ointment to the skin, once the container 10 is emptied, the entire assembly can be discarded or recycled depending on the construction materials.

Figure 9:
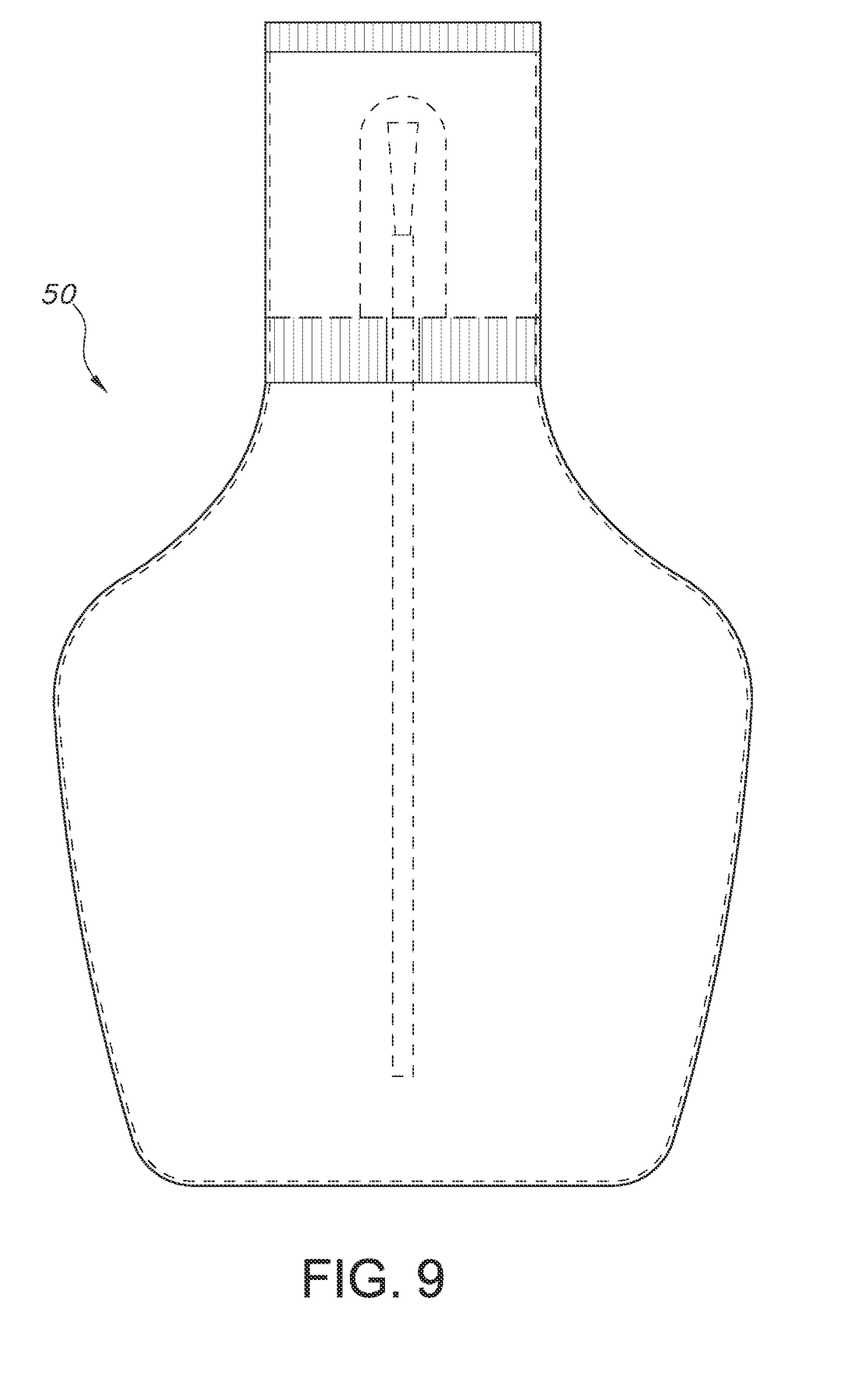
FIG. 9 is a front sectional view of an alternative embodiment of the disposable topical application system of the present invention.

As seen in FIG. 9, the shape and dimensions of the various components are not limited to the preferred embodiment of the invention. The disposable topical application system 50 can be designed and manufactured in a multitude of arrangements to accommodate the best practices of applying the dispensable product on a desired surface.

As seen in FIGS. 13-18, an alternative embodiment of the disposable topical application system 10 teaches a different method for the egress of the dispensable product. A sealed edge 12 of suitable configuration extends across the top of the body of the fluid-holding portion 22 with only an opening formed by the neck portion or distal end 20 of the elongated applicator 16 and provides an upper barrier to the fluid within the container 10 as defined by the aforementioned second cavity 15. A central fluid delivery aperture 23' in the wall of the cylindrical applicator 16 provides a fluid pathway out of the fluid-holding portion 22 of the container 10 the central bore of the applicator 16. The aperture 23' is strategically disposed at the neck 20 of the applicator 16 near to the top edge seal, so as to encourage maximum dispensing with the introduction of gravity when the disposable topical application 11 system is inverted for use. As seen in FIGS. 13-18, the aperture 23' is created when force is exerted on the diagonal rupture line 21' in the elongated applicator 16. This obviates the need for a compromisable aperture cover 21 taught in the preferred aforementioned embodiment. The elongated applicator 16 is still generally tubular in shape so as to define a central fluid passage with the inclusion of the diagonal rupture line 21' that creates the aperture 23' for egress. The distal end of the applicator 16 features an aperture capable of permitting the passage of fluid therein. In the preferred embodiment, the contents of the container 10 pass through the aforementioned aperture and subsequently impregnate the tip of the application. Depending on the construction of the applicator, the portion of the applicator in the sealed container aids manual dexterity when the disposable topical application system is in use.

Figure 18:
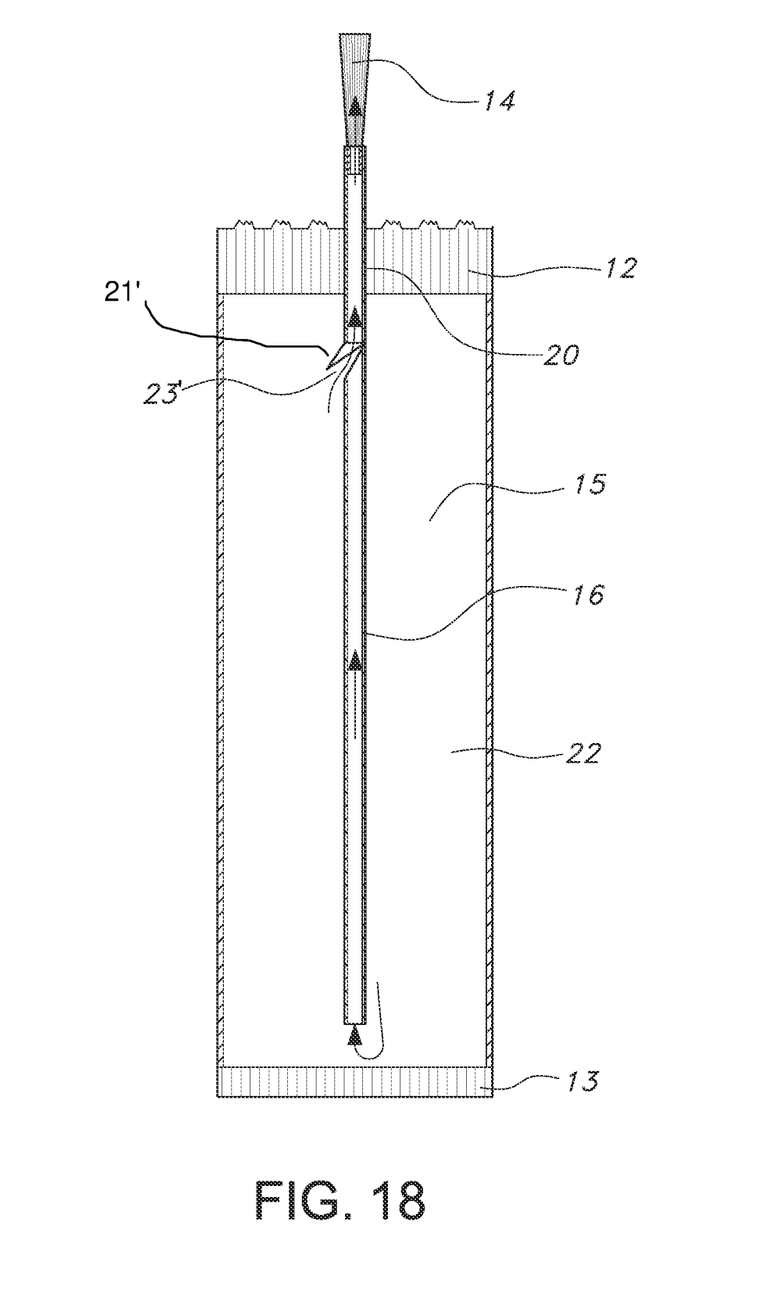
FIG. 18 is a front sectional view of showing the egress of the contents of an unsealed alternative embodiment of the disposable topical application system of the present invention.

A generally diverse applicator tip 14 can be conveniently formed at the proximate end 20 of the hollowed applicator 16 secured within the container 10 by sealing the top edge 12 of the fluid-holding portion 22 using a suitable lamination or other bonding process. As seen in FIGS. 15-18, the alternative embodiment teaches a tip 14 having a brush configuration defined by a plurality of bristles. As seen in FIG. 18, once urged from the fluid-holding portion 22 via manual force or squeezing (e.g., see FIG. 6), the fluid is urged through the aperture 23 in the applicator 16 and subsequently impregnates the brush tip 14 upon exit the proximate end 20 of the applicator 16 as seen by the directional arrows in FIG. 8. Inclusion of various tip configurations which might include the use of additional mounting arrangements for a spatula tip 31 or sponge tip 32 are shown in FIGS. 11 and 12, respectively. The applicator tip 14 receives the fluid via the fluid pathway provided by the aperture 23. The applicator tip is sufficiently porous to the fluid and can be formed as a foam member using a suitable polymeric (e.g., urethane) open cell foam. Moreover, the applicator tip can be fashioned as a dropper (not shown) for precision placement of the dispensable product (e.g., eye drops).

Alternative embodiments of the present invention also teach the inclusion of a removable cap. As with the rupturable seal in the design of the preferred embodiment, the premature evacuation of the dispensable product through the applicator is prevented by introduction of an easily removable cap or seal disposed on the tip of the elongated applicator. Inadvertent squeezing of the fluid-holding portion may cause unwanted impregnation of the applicator tip. The orifice at the proximate end is covered with a removable cap, rupturable seal, or aluminum seal with a pull tab to facilitate prompt removal. This alternative embodiment may require the brush, sponge, spatula, and like applicator heads to be detachable to access said orifice at the proximate end of the applicator. The additional cost of this loss prevention feature is offset by increased assurance the proper amount or dosage is always dispensed. Accordingly, an applicator tip with a removable (or rupturable) seal or removable cap has been disclosed.

Still another alternative embodiment of the disposable topical application system of the present invention teaches a different dispensing system. In this alternative embodiment, the length of the applicator is shortened to lay flush with the crown of the top sealed edge of the fluid-holding portion and defining an orifice at the bottom of the applicator. The top sealed edge now has generally chevron configuration. Hence, when the disposable topical application system is inverted, the generally chevron configuration assures all the dispensable product is urged towards that crown and through the orifice for subsequent dispensing. The shortened applicator may slightly inhibit dexterity for those users with larger hands, but the shortened applicator is a cost-saving measure that increases the efficiency of the dispensing. The cap or sealed opening system in conjunction with the applicator can be selectively manipulated to break the seal when it is desired to use the disposable topical application system and apply its contents to a desired surface. When the proximate end is sealed with a penetrable cover, a pen tip or other pointy object can be thrust in the orifice to break the seal and permit egress of the dispensable product as taught herein.

Yet another alternative embodiment teaches a disposable topical application system that is still disposable, but refillable with dispensable product in a sterile manner. This alternative embodiment affords a user multiple uses before discarding the disposable. Additional dispensable product can be introduced through the central bore of the applicator by the user. For example, it may be possible to form the opening as a small hole (not shown) that receives a cannula through which the dispensable product is injected into the fluid-holding portion of the container. The design of the disposable topical application system for future fluid introduction processes is not limited to what is taught here and generally understood by a person having ordinary skill in the art to be within the scope of this invention.

While the preferred embodiments of the disposable topical application system have been described in detail in this specification and drawings, it should be apparent that modifications and variations thereto are possible, all of which fall within the true spirit and scope of the invention. With respect to the above description then, it is to be realized that the optimum functionality for the components of the invention, to include variations in dimensions and functionality are deemed readily apparent and obvious to one skilled in the art, and all equivalent relationships to those illustrated in any appendices, drawings, images, and embodiments described in the specification are intended to be encompassed by the present embodiments of the invention. Moreover, the scope of this invention anticipates the application of the above teachings to other goods/services not traditionally available to users of the present invention. Hence, the present invention has been described above in terms of specific embodiments, it is to be understood that the invention is not limited to these disclosed embodiments.

The invention claimed is:
1. A disposable topical application system comprising:
a) a housing unit including a first section and a second section connected to said first section, said second section being selectively detachable from said first section;
wherein a fluid being contained within said first section of the housing unit;
b) an applicator disposed within the housing unit extending between said first section and said second section, the applicator including an elongated cylindrical hollow tube having a proximate end disposed within the second section and a distal end located within the first section, the elongated cylindrical hollow tube including an opening in a side wall of the tube between the proximate and distal ends within the first section that extends only partially around a circumference of the tube such that the proximal and distal ends of the tube remain connected;
c) a tip member attached to said applicator in said second section of said housing, said tip member designed and configured to be in fluid communication with the interior of said tube; wherein upon use of manual force, said second section being separable from said first section, exposing the tip member and maintaining the fluid within the first section; and
wherein, on demand, upon a use of manual force, the fluid is moved from the first section through said tube and distributing via the tip to a place of application by a user;
d) a frangible cover disposed over said opening; wherein the frangible cover disengages from the tube exposing the opening to the fluid within the first section upon applying a bending force to the tube.
2. The disposable topical application system according to claim 1, wherein said tip member includes a brush comprised of a plurality of bristles; said brush receiving fluid therethrough from said tube, distributing through said bristles, and dispensing onto the application location.

3. The disposable topical application system according to claim 1, wherein said tip member includes a sponge comprised of a porous material with elasticity; said sponge receiving fluid therethrough from said tube, distributing through said porous material, and dispensing onto the application location.

4. The disposable topical application system according to claim 1, wherein said tip member includes a spatula comprised of a hollow and flared end; said spatula receiving fluid therethrough from said tube, distributing through said hollow and flared end, and dispensing to the application location.

* * * * *